United States Patent [19]

Goldstein

[11] 4,347,189

[45] Aug. 31, 1982

[54] PROCESS FOR SEPARATING 1,4 CINEOLES FROM 1,8 CINEOLES

[75] Inventor: Theodore P. Goldstein, Yardley, Pa.

[73] Assignee: Mobil Oil Corporation, New York, N.Y.

[21] Appl. No.: 262,165

[22] Filed: May 11, 1981

[51] Int. Cl.$^3$ .................. C07D 311/02; C07D 307/77
[52] U.S. Cl. ..................................... 549/397; 549/463
[58] Field of Search ......................... 260/345.1, 346.22

[56] References Cited

U.S. PATENT DOCUMENTS

| | | | |
|---|---|---|---|
| 2,315,986 | 4/1943 | Scrutchfield | 260/345.1 |
| 3,923,837 | 12/1975 | Davis | 260/346.22 |
| 4,096,163 | 6/1978 | Chang et al. | 518/713 |

OTHER PUBLICATIONS

Sand, Molecular Sieves, Society of Chemical Industry, 1968, pp. 71–77.

*Primary Examiner*—Nicky Chan
*Attorney, Agent, or Firm*—Charles A. Huggett; Michael G. Gilman; Charles J. Speciale

[57] ABSTRACT

A method of separating 1,4 cineole from a mixture containing 1,4 and 1,8 cineoles wherein the mixture is contacted with a zeolite having a constraint index of from 0.2 to 12 and having port sizes of approximately 6.7–7.0 angstroms. This causes the 1,4 cineole to be sorbed into the zeolite while the 1,8 cineole is excluded. The zeolite is then separated from the 1,8 cineole so that the 1,4 cineole may be desorbed from the zeolite. This desorption may be accomplished by heating the zeolite to a temperature above the boiling point of the cineole or by liquid phase displacement.

17 Claims, No Drawings

PROCESS FOR SEPARATING 1,4 CINEOLES FROM 1,8 CINEOLES

BACKGROUND OF THE INVENTION

1. Field of the Invention

This invention relates to a method of separating cineoles, and more particularly, to a method of separating 1,4 cineole from a mixture of 1,4 and 1,8 cineoles by use of a zeolite molecular sieve. The structural formulas for 1,4 and 1,8 cineoles are shown below.

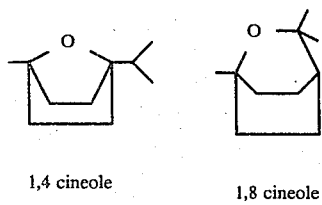

1,4 cineole      1,8 cineole

Cineoles (also known as eucalyptols) have been found to have a wide variety of uses. Muller, et al. have discovered that cineole may be used to retard the respiration of herb roots and inhibit the growth of seedlings. Bull. Torrey Bot. Club 1968, 95(5), 415–22.

Dassler and Dube found that 1,4 cineole was a useful insecticide for use against flies, 1,8 cineole, however, was useful against bark-beetles, but did not show the same results against flies, *Anz. Schadlingskunde* 30, 86–8(1967).

Dodson, et al. have described 1,8 cineole as an attractant for male euglossine bees. The 1,8 cineole was found to be a component in orchid fragrances. *Science* 1969, 164(3885), 1243–9.

Cineoles also have uses as medicinal compositions. This is shown by Pozzo, et al. who describe a method of determining the amount of eucalyptol in pharmaceutical syrups and suppositories. Boll. Chim. Farm. 1969, 108, 47–56. Stamm, et al. describe the optimization of retaining eucalpytol by use of different absorbents in compressed tablets. *Bull Soc. Pharm. Strasbourg* 1970 13(2) 89–95.

In Ger. Offen. No. 2,213,993 Sept. 27, 1973) and British Pat. No. 1,343,561, Igimi et al. described essentials oils which were found to be useful in dissolving gallstones in bile liquid. Cineole was listed as an example of one of these essential oils. French Pat. No. 1,495,547 describes eucalpytol as a useful component in compositions for regulating the activity of sebaceous glands. Lobel, U.S. Pat. No. 3,105,793, includes eucalpytol in a composition useful for reducing the side effects of injectable antibiotics. Cineole has been found to inhibit the oxygen uptake by mitochrondria of seedlings. Bull. Torrey Bot. Club 1969, 96(1), 89–96.

More importantly, eucalyptol has been found to effect the metabolism of drugs in humans. *Eur. J. Pharmacol,* 1970, 9(3), 326–6; *Biochem. Pharmacol.* 1969, 18(9), 2081–5. These metabolic effects can be very important in the detoxification of certain compounds in humans.

Although mixtures of 1,4 and 1,8 cineoles may be useful, it is generally considered that the separated compounds are more valuable than the mixture. The difficulty in separating such mixtures can be seen by comparing some of the more important physical properties of the two compounds.

| Property | 1,4 cineole | 1,8 cineole |
| --- | --- | --- |
| Molecular weight | 154.25 | 154.25 |
| Boiling point (760mm Hg) | 173–4° C. | 176.4° C. |
| Density | $0.8997^{20}$ | $0.9267^{20}$ |

Each cineole is practically insoluble in water and is miscible with alcohol, chloroform, ether, glacial acetic acid and other hydrocarbon solvents in general.

For further physical, chemical and pharmaceutical properties of cineoles, see *Izvest, Akad. Nauk Kazakh. S.S.R. No. 118, Ser. Khim., No. 6, 90–106(1953).

Because of the similarities of the properties, it is apparent that conventional separation methods, such as distillation or phase separation, are not suitable for the separation of the cineoles.

Cineoles are generally prepared by treating bicyclic monoterpene hydrocarbons, dipentenes, or isoprenes with mineral acids such as sulphuric acid. Japanese Patent 68-24,674; Vestsi Akad. Navuk B. SSR, Ser. Khim. Navuk 1974, (5); 61–4; *Vestsi Akad. Navuk B. SSR, Ser. Khim, Navuk* 1974, (6), 17 ∝ 19; and Japanese Patent 68-24,186. These methods result in final mixtures containing similar amounts of 1,4 and 1,8 cineoles, along with other products such as menthadienes, cymenes and terpinenes. Cineoles are also available from natural sources, such as oils of wormwood and eucalyptus. Mixtures of cineole isomers can be synthetically obtained from limonene, terpin hydrates, turpentine and oil of turpentine.

2. Description of the Prior Art

Previous methods of separating mixtures of cineoles have been difficult and unwieldy. One process, described in Japanese Patent No. 69-07,340 (Mar. 31, 1969) by Matsuhara et al involves treating a crude mixture including 1,4 and 1,8 cineoles with thiourea. The 1,4 cineole then separates as an adduct. This process is limited to liquid phase operations.

U.S. Pat. Nos. 2,459,432 and 2,459,433, both to Johnson, disclose a method for separating cineoles from hydrocarbons. A cineole-containing hydrocarbon mixture is treated with phenol, resulting in three azeotropic mixtures which are separatable from each other by distillation: hydrocarbon and phenol; 1,4-cineole and phenol; and 1,8 cineole and phenol. The 1,8-cineole azeotrope boils higher than the 1,4-cineole azeotrope. Fractional steam distillation may be used to recover each of the cineoles from its respective azeotrope.

Davis, in U.S. Pat. No. 3,923,837 describes an extraction process for removing cineoles from a terpene fraction by use of a strong mineral acid, such as sulphuric. The cineoles are removed into the acid component. However, both 1,4 and 1,8 cineoles are removed by the acid extraction.

Okuda, Japanese Pat. No. 1172-50 describes isolating cineoles from other essential oils. 2-naphthol is added to white camphor oil and centrifuged. Sodium hydroxide is added to the formed compound, resulting in an oily layer which is steam-distilled to obtain the cineoles.

SUMMARY OF THE INVENTION

It is an object of this invention to provide a method of separating 1,4 cineole from a mixture containing 1,4 and 1,8 cineoles.

It is a further object of this invention to provide a method of separating cineoles which is simple to use and economical.

It is a still further object of this invention to provide a method of separating cineoles which is useful under a wide variety of conditions.

The above objects and others are obtained by providing a method wherein a zeolite having a specific constraint index is used so that 1,4 cineole is sorbed from a mixture, while 1,8 cineole is not sorbed. The zeolite with the sorbed 1,4 cineole is separated from the mixture, and the 1,4 cineole is then sorbed by methods such as liquid or vapor phase desorption.

DETAILED DESCRIPTION OF THE INVENTION

The method of separating 1,4 and 1,8 cineoles of the present invention involves contacting a mixture containing these two cineoles with a zeolite molecular sieve chosen such that only 1,4 cineole is sorbed onto the zeolite. The specific zeolites which may be used in the present invention will be described later. The zeolite can easily be separated from the rest of the mixture after sorption has been effected. After separation, the 1,4 cineole can be desorbed from the zeolite, and the zeolite can be reactivated, providing an efficient and economical process.

An important characteristic of the zeolites used in this invention is that the crystal structure of these zeolites provides constrained access to, and egress from spaces within the crystal structure. One useful method of determining this access is by calculating the "constraint index", measured as follows. A sample of the zeolite is crushed to a particle size similar to that of coarse sand and mounted in a glass tube. The zeolite is treated with a stream of air at approximately 1,000° F. for at least 15 minutes. After this, the zeolite is flushed with helium and the temperature is reduced to between 550 and 950° C. A mixture of hydrocarbons consisting of equal weights of N-hexane and 3-methylpentane, diluted with helium to give a helium to hydrocarbon mole ratio of 4:1, is passed over the zeolite at a rate of 1 volume of liquid hydrocarbon per volume of zeolite per hour. Afer 20 minutes, a sample of the effluent is taken and analyzed, for example by gas chromatography, to determine the fraction of each original hydrocarbon unchanged after being passed through the zeolite. The following formula is used to calculate the constraint index:

$$\text{Constraint Index} = \frac{\log_{10} \text{(fraction of n-hexane remaining)}}{\log_{10} \text{(fraction of 3-methylpentane remaining)}}$$

Thus, the constraint index approximates the ratio of the "cracking" rate constants for each of the hydrocarbons, and thus indicates the access of each hydrocarbon into the free space within the crystalline structure of the zeolite. This process is also described in U.S. Pat. No. 4,097,543 to Haag, et al. which is incorporated herein by reference.

For the present invention, zeolites having a constraint index of from 0.2 to 12 are preferred. The zeolites should also have a silica to alumina mole ratio of at least about 12. It is also important that these zeolites, examples of which are mordenite, ptilolite, NaD, Linde Type L, Mazzite, ZSM-4, Omega, Gmelinite, S zeolite, ZSM-5, ZSM-11, Faujasite, Linde Type X and Linde Type Y, have port sizes of approximately 6.7 to 7.0 angstroms. The molecular dimensions of 1,4 cineole are approximately $10 \times 6.5 \times 5.5$ angstroms, while those of the 1,8 cineole are about $8.5 \times 8.5 \times 6.5$ angstroms. Thus, the 1,4 cineole may pass through the ports, while the 1,8 cineole is excluded.

To separate 1,4 cineole from a mixture containing 1,4 and 1,8 cineoles, the mixture is contacted with a zeolite described above in either a batch or continuous process. The mixture can consist only of 1,4 and 1,8 cineoles, or it may also include a hydrocarbon solvent, or it may be the process stream from one of the earlier described methods of producing cineoles. In the continuous process, the zeolite may be present in either fixed or fluidized beds. The 1,4 cineoles is sorbed by the zeolite and thus effectively removed from the mixture. After the mixture is separated from the zeolite, the sorbed 1,4 cineole can be recovered from the zeolite by any of several methods. For example, the cineole may be displaced from the zeolite by use of an alcohol such as methanol, ethanol or isopropanol, alcohol-water mixtures, acetone, acetone-water mixtures, or other solvents. Desorption may also be accomplished in the vapor phase by heating the zeolite containing the cineole to a temperature of approximately 150° to 200° C. with an apparatus utilizing a suitable condenser to collect the desorbed cineole as a liquid product.

More specifically, a mixture containing equal weights of 1,4 and 1,8 cineoles is contacted with synthetic mordenite in a stirred batch reactor. The zeolite is prepared for use by calcining in a stream of air at 500° C. for one hour. The relative amount of the zeolite used is such that the sorptive capacity of the zeolite exceeds the weight of 1,4 cineole in the mixture, thus achieving maximum separation efficiency. For example, 100 grams of a synthetic mordenite zeolite sorbs about 5 grams of 1,4 cineole at room temperatures and one atmosphere. Of course, the sorptive capacities of other zeolites under different operating conditions can be readily determined by standard techniques.

For liquid phase sorption temperatures ranging from ambient to approximately the boiling point of the cineoles may be used. It is preferred that a temperature of approximately 100° C. and a pressure of 760 mm Hg be used. Under these conditions, approximately 100 grams of zeolite are used for each gram of 1,4 cineole. Since the sorption of the 1,4 isomer by the zeolite increases the relative amount of 1,8 cineole in the liquid phase, the progress of the separation process may be monitored by any suitable analytical procedure, such as gas chromatography, to determine the extent of separation and to optimize operating conditions.

After the sorption is completed, the zeolite is physically separated from the mixture by a process such as filtration, leaving a liquid phase enriched in the 1,8 cineole. As described earlier, the 1,4 cineole can be isolated from the zeolite by vapor phase desorption wherein the zeolite is heated to a temperature greater than the cineole boiling point, followed by condensation of the cineole vapors. When vapor phase desorption is utilized, it is preferred that this be carried out in an inert atmosphere to avoid oxidation or other degradation of the cineole recovered. Desorption may also be accomplished by displacing the 1,4 cineole with a more strongly sorbed material which is easily separated from the cineole. For example, when methanol is used to displace the cineole, the cineole can be isolated from methanol by distillation.

After desorption of the cineole, the zeolite can be reused for successive separations. The zeolite can be reactivated for this purpose by heating it in a stream of inert gas or air to a temperature high enough to drive off various organics sorbed by the zeolite and remaining in the crystalline structure. Periodically, it may be necessary to regenerate the zeolite by calcination in air or pure oxygen at temperatures of approximately 500° C. in order to remove extremely high boiling or refractory organics. This allows removal of these contaminants by combustion.

The above described method is also useful for separating 1,4 cineole from a process stream such as that obtained from the previously described methods of preparing the cineoles. Also, the zeolite may be present in the form of a fixed or fluidized bed for use in either a batch or continuous process.

It is also contemplated that a vapor phase sorption of cineoles rather than liquid phase can be used. This vapor phase sorption is suitable for use with any of the processes described above, and similar conditions would be used except that the sorption step would be carried out at a temperature near the boiling point of the cineoles.

It is apparent that modifications in the above description can be made by those skilled in the art without departing from the scope and spirit of the invention, which is defined by the following claims.

The embodiments of the invention in which an exclusive property or privilege is claimed are defined as follows:

1. A method of separating 1,4 cineole from a mixture comprising 1,4 and 1,8 cineoles comprising:
   contacting said mixture with a zeolite having a constraint index of from 0.2 to 12 and port sizes of approximately 6.7–7.0 angstroms such that said 1,4 cineole is sorbed into said zeolite;
   separating said zeolite and said mixture; and
   desorbing said 1,4 cineole from said zeolite.

2. The method of claim 1, wherein said zeolite is selected from the group consisting of mordenite, ptilolite and NaD.

3. The method of claim 1, wherein said zeolite is selected from the group consisting of Linde Type L, Mazzite, ZSM-4, Omega, Gmelinite, S zeolite, ZSM-5, ZSM-11, Faujasite, Linde Type X and Linde Type Y.

4. The method of claim 1, 2 or 3 wherein said desorbing is a vapor phase desorption.

5. The method of claim 1, 2 or 3 wherein said desorbing is a liquid phase desorption.

6. The method of claim 5 wherein said liquid phase desorption is accomplished by immersing said zeolite in an alcohol selected from the group consisting of methanol, ethanol and isopropanol.

7. The method of claim 1 wherein said mixture further comprises a hydrocarbon solvent.

8. The method of claim 1 wherein said mixture is a process stream obtained during production of 1,4 and 1,8 cineoles.

9. The method of claim 1 wherein said zeolite is contacted with said mixture as a batch.

10. The method of claim 1 wherein said zeolite is present as a fixed bed.

11. The method of claim 1 wherein said zeolite is present as a fluidized bed.

12. The method of claim 10 or 11 wherein said method is a continuous process.

13. The method of claim 1 wherein prior to contact with said zeolite, said cineoles are in the vapor phase.

14. A method of separating 1,4 cineole from a mixture comprising 1,4 and 1,8 cineoles comprising:
   contacting said mixture with mordenite having a constraint index of from 0.2 to 12 and having port sizes of approximately 6.7–7.0 angstroms such that said 1,4 cineole is sorbed into said mordenite, the amount of said mordenite being about 100 grams per each gram of 1,4 cineole, said contacting occurring under conditions of about 100° C. and 760 mm Hg;
   separating said mordenite from said mixture; and
   desorbing said 1,4 cineole from said mordenite.

15. The method of claim 14, wherein said desorbing is a vapor phase desorption.

16. The method of claim 14, wherein said desorbing is a liquid phase desorption.

17. The method of claim 16, wherein said liquid phase desorption is accomplished by immersing said mordenite in an alcohol selected from the group consisting of methanol, ethanol and isopropanol.

* * * * *